US008845715B2

(12) United States Patent
Sherif

(10) Patent No.: US 8,845,715 B2
(45) Date of Patent: Sep. 30, 2014

(54) TOTAL AORTIC ARCH RECONSTRUCTION GRAFT

(76) Inventor: Hisham M. F. Sherif, Newark, DE (US)

( * ) Notice: Subject to any disclaimer, the term of this patent is extended or adjusted under 35 U.S.C. 154(b) by 812 days.

(21) Appl. No.: 12/540,615

(22) Filed: Aug. 13, 2009

(65) Prior Publication Data

US 2010/0042201 A1    Feb. 18, 2010

Related U.S. Application Data

(60) Provisional application No. 61/189,226, filed on Aug. 18, 2008.

(51) Int. Cl.
*A61F 2/07*    (2013.01)
*A61F 2/90*    (2013.01)
*A61F 2/06*    (2013.01)
*A61F 2/848*   (2013.01)

(52) U.S. Cl.
CPC ............. *A61F 2/07* (2013.01); *A61F 2002/075* (2013.01); *A61F 2/06* (2013.01); *A61F 2002/8486* (2013.01); *A61F 2002/8483* (2013.01); *A61F 2/90* (2013.01)
USPC .......... 623/1.16; 623/1.36; 623/1.23; 606/153

(58) Field of Classification Search
USPC ............................................... 623/1.13, 1.36
See application file for complete search history.

(56) References Cited

U.S. PATENT DOCUMENTS

| | | | |
|---|---|---|---|
| 4,798,606 A | 1/1989 | Pinchuk | 623/1 |
| 5,035,709 A | 7/1991 | Wieting et al. | 623/2 |
| 5,123,919 A | 6/1992 | Sauter et al. | 623/2 |
| 5,156,621 A * | 10/1992 | Navia et al. | 623/2.12 |
| 5,163,954 A | 11/1992 | Curcio et al. | 623/2 |
| 5,397,346 A | 3/1995 | Walker et al. | 623/2 |
| 5,824,064 A | 10/1998 | Taheri | 623/2 |
| 5,843,178 A | 12/1998 | Vanney et al. | 623/2 |
| 5,855,603 A | 1/1999 | Reif | 623/2 |
| 5,891,195 A | 4/1999 | Klostermeyer et al. | 623/2 |
| 6,039,183 A | 3/2000 | Rudnick et al. | 206/570 |
| 6,045,576 A | 4/2000 | Starr et al. | 623/2 |

(Continued)

FOREIGN PATENT DOCUMENTS

CN    201026247    *    2/2008    ................ A61F 2/06

OTHER PUBLICATIONS

Brochure, "E-vita Open the Endoluminal Stentgraft System for Open Heart Surgery" (JOTEC GmbH 2005).

(Continued)

*Primary Examiner* — Thomas J Sweet
*Assistant Examiner* — Rebecca Preston
(74) *Attorney, Agent, or Firm* — James C. Lydon

(57) ABSTRACT

A total aortic arch reconstruction graft, including a first, hollow cylindrical segment in the shape of an aortic arch, a second, hollow cylindrical segment having a first end joined to the second end of the first segment, and a second end adapted to be inserted into the descending aorta of a patient, the second segment having an expandable outer wall covered with an expandable stent, and a collar having a diameter larger than the diameter of said first segment, the collar located at a juncture where the first end of the second segment is joined to the second end of the first segment, with a plurality of separate, non-absorbable double-armed sutures pre-attached to the collar. A surgical procedure for total replacement of a patient's aortic arch is also disclosed.

15 Claims, 3 Drawing Sheets

(56) References Cited

U.S. PATENT DOCUMENTS

| | | | |
|---|---|---|---|
| 6,187,033 B1 | 2/2001 | Schmitt et al. | 623/1 |
| 6,299,575 B1 | 10/2001 | Bolling | 600/16 |
| 6,499,487 B1 | 12/2002 | McKenzie et al. | 128/898 |
| 6,685,625 B2 | 2/2004 | Gabbay | 600/36 |
| 6,770,090 B2 * | 8/2004 | Gantt et al. | 623/1.35 |
| 6,773,457 B2 | 8/2004 | Ivancev et al. | 623/1.28 |
| 6,918,925 B2 | 7/2005 | Tehrani | 623/1.11 |
| 6,936,067 B2 * | 8/2005 | Buchanan | 623/2.28 |
| 7,232,459 B2 | 6/2007 | Greenberg et al. | 623/1.13 |
| 2004/0049262 A1 * | 3/2004 | Obermiller et al. | 623/1.15 |
| 2007/0167955 A1 * | 7/2007 | Arnault De La Menardiere et al. | 606/108 |
| 2008/0109058 A1 * | 5/2008 | Greenberg et al. | 623/1.11 |
| 2009/0093873 A1 * | 4/2009 | Navia | 623/1.23 |
| 2010/0185279 A1 * | 7/2010 | Shad | 623/2.38 |

OTHER PUBLICATIONS

Brochure, "Gelweave™ Thoracic and Thoracoabdominal Graft Geometries" (Vascutek Terumo undated).

\* cited by examiner

TOTAL AORTIC ARCH RECONSTRUCTION GRAFT

This application claims the benefit of U.S. provisional application No. 61/189,226, filed Aug. 18, 2008, whose disclosure is incorporated by reference herein in its entirety.

BACKGROUND OF THE INVENTION

The present invention relates to vascular grafts. More particularly, this invention relates to a graft suitable for replacement of the entire aortic arch.

Replacement of the entire aortic arch presents a significant challenge to the cardiac surgeon. Exposure of the descending aorta is much more difficult than exposure of the ascending aorta, which is itself difficult to expose. Accordingly, the vast majority of aortic surgical techniques call for inserting a folded graft inside the descending aorta by suturing the edge of the folded graft first to the rim (cut edge) of the descending aorta, then inverting the graft to straighten it and let it fall within the descending aorta, followed by expanding and fixing the graft against the descending aortic inner wall.

The folded graft procedure summarized above requires a fairly long period of complete deep hypothermic systemic cardiac arrest, in which the patient's body is cooled to a deep level and blood circulation to the entire body is stopped. Surgeons attempt to minimize the duration of deep hypothermic systemic cardiac arrest for obvious reasons.

However, bleeding from the suture line where the graft has been attached to the descending aorta is a common problem. The need to control bleeding often requires maintaining the patient on deep hypothermic arrest for a longer period of time, which increases the risk of neurologic and other organ injury.

U.S. Pat. No. 6,770,090 discloses an anatomically curved aortic arch graft. The graft's curvature is said to better conform the graft to the natural curvature of the aortic arch without kinking.

U.S. Pat. No. 6,187,033 discloses an aortic arch graft in which three tubes adapted for attachment to the brachiocephalic artery, left common carotid artery and left subclavian artery are each joined to the elongate tubular main wall of the graft by means of a common tubular branch wall extending laterally from the tubular main wall.

"E-vita Open The Endoluninal Stentgraft System for Open Heart Surgery" (JOTEC GmbH 2005) discloses a graft having two segments: a short segment ("cuff") of a conventional vascular graft which is joined to a stent-graft. The cuff is designed to be attached to another, separate graft which replaces the aortic arch and the ascending aorta. The joint between the first segment and the stent-graft is reinforced with a metal ring and sutures to maintain a stable, impermeable connection between the first segment and the stent-graft. This graft relies upon its stent section to fix itself against the descending aortic wall, and can suffer from the problem of bleeding from the suture line where the graft is attached to the descending aorta.

"Gelweave™ Thoracic and Thoracoabdominal Graft Geometries" (Vascutek Undated) discloses a 4 branched graft having a collar designed to compensate for differences in diameter between the distal aorta and the graft. The collar functions as a sewing ring, and must be trimmed to fit the patient's aorta, which undesirably increases the duration of deep hypothermic arrest. Secure placement of the junction between the two graft segments at the open end of the descending aorta is difficult due to the discrepancy between the trimmed collar's diameter and that of the graft. Moreover, conventional sutures must be used to attach this graft, which increases the probability the suture line will bleed.

U.S. Pat. No. 5,163,954 discloses a suture ring for heart valve prostheses having an internal surface or coating which is substantially water repellant, and an outer surface or coating which is substantially hydrophilic and porous.

SUMMARY OF THE INVENTION

In one aspect, the present invention relates to a total aortic arch reconstruction graft, comprising a) a first, hollow cylindrical segment in the shape of an aortic arch and having two opposed ends and a pre-determined diameter,
  said first segment having three hollow cylindrical side branches in communication therewith, said three side branches in the same or substantially the same plane with one another and adapted to be joined to a patient's left subclavian artery, left common carotid artery and innominate artery, respectively,
  said first segment having a fourth hollow cylindrical side branch adapted to be joined to a perfusion device;
  a first end of said first segment being adapted to be joined to the ascending aortic wall of a patient;

b) a second, hollow cylindrical segment having two opposed ends,
  a first end of said second segment being joined to the second end of said first segment,
  a second end of said second segment adapted to be inserted into the descending aorta of a patient, said second segment having an expandable wall whose outer surface is at least partially covered with an expandable open-mesh stent, said stent having means for attaching said second segment to an internal surface of a patient's descending aorta,
  an initial diameter of said second end of the second segment being smaller than the diameter of said first segment;

c) a collar having a diameter slightly larger than the diameter of said first segment, said collar located at a juncture where the first end of said second segment is joined to the second end of said first segment, and having means for attaching said collar to a patient's open aorta.

DETAILED DESCRIPTION OF THE PREFERRED EMBODIMENTS

Figure 1:
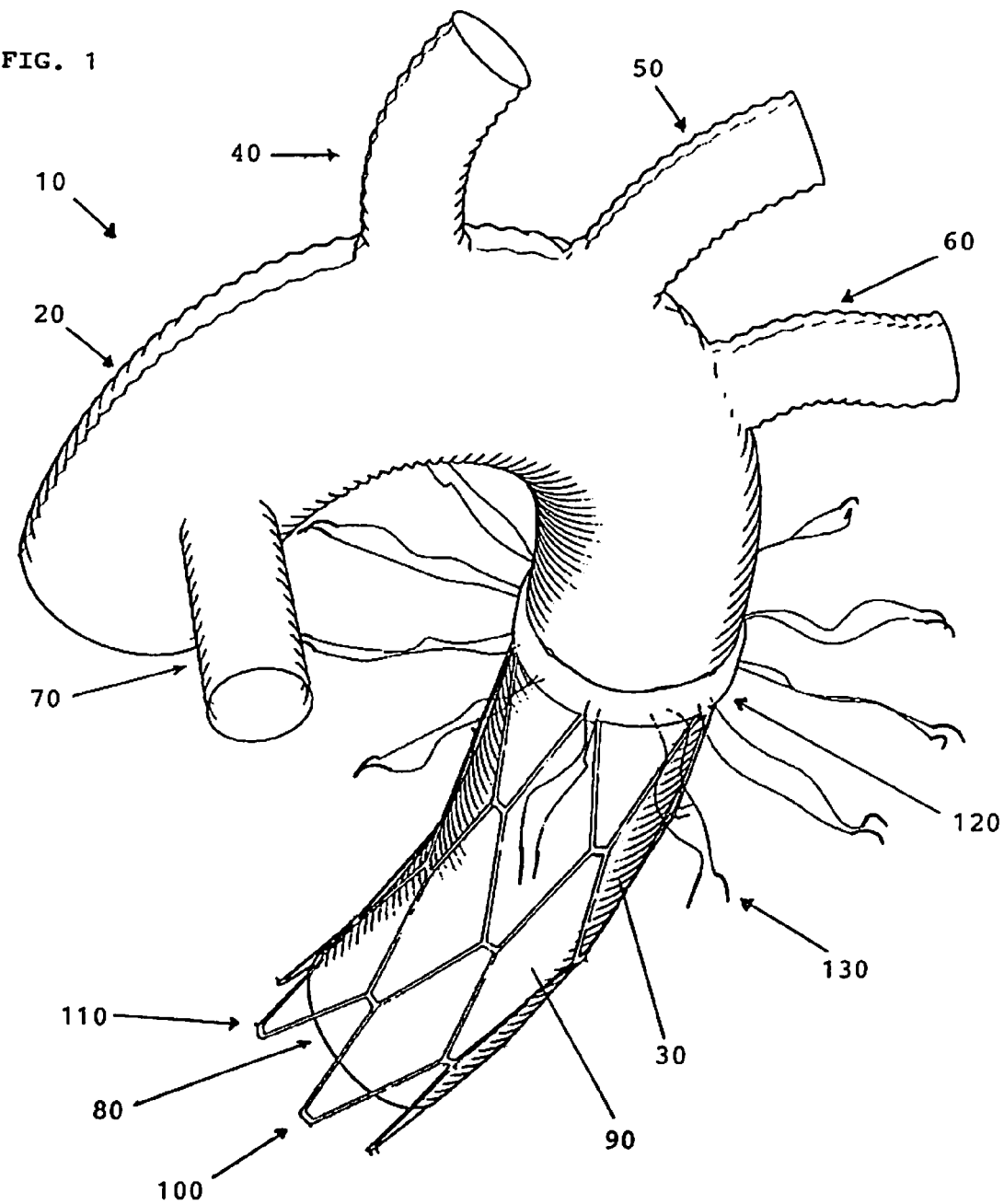
FIG. 1 is a perspective view of a preferred embodiment of the total aortic replacement graft of the present invention.

The inventor has discovered the aorta may be more easily and quickly replaced using a reconstruction graft comprising a) a first, hollow cylindrical segment in the shape of an aortic arch and having two opposed ends and a pre-determined diameter,
  said first segment having three hollow cylindrical side branches in communication therewith, said three side branches in the same or substantially the same plane with one another and adapted to be joined to a patient's left subclavian artery, left common carotid artery and innominate artery, respectively, said first segment having a fourth hollow cylindrical side branch adapted to be joined to a perfusion device;
a first end of said first segment being adapted to be joined to the ascending aortic wall of a patient;
b) a second, hollow cylindrical segment having two opposed ends,
a first end of said second segment being joined to the second end of said first segment,
a second end of said second segment adapted to be inserted into the descending aorta of a patient,
said second segment having an expandable wall whose outer surface is at least partially covered with an expandable open-mesh stent, said stent having means for attaching said second segment to an internal surface of a patient's descending aorta,
an initial diameter of said second end of said second segment being smaller than the diameter of the first segment;
c) a collar having a diameter larger than the diameter of said first segment, said collar located at a juncture where the first end of said second segment is joined to the second end of said first segment, and having means for attaching said collar to a patient's open descending aorta.

The total aortic replacement graft should be made of materials selected for lifetime durability as well as biocompatibility. In a preferred embodiment, the first and second segments are both made of a material selected from the group consisting of nylon, polyester, polyolefin, polyurethane, polytetrafluoroethylene, mixtures thereof, and equivalent polymers. These materials can be used in the form of monofilament and multifilament yarns.

The graft's material is preferably woven, and can be flat woven using any known weave pattern, including simple weaves, basket weaves, twill weaves, velour weaves and the like. For example, the graft may be woven using a flat plain tubular weave pattern with about 100-200 warp yarns per inch per layer and about 70-120 fill yarns per inch per layer. Preferably, the graft is woven with about 170-190 warp yarns per inch per layer and about 86-90 fill yarns per inch per layer. The wall thickness of the graft may be any conventional useful thickness, but is desirably no greater than about 1.0 mm. A useful wall thickness includes, but is not limited to, from about 0.10 mm to about 0.75 mm.

In a still more preferred embodiment, at least one of the segments is made from a polyester selected from the group consisting of woven polyester, double-velour woven polyester, knitted polyester, albumen coated woven polyester and albumen coated knitted polyester.

The first segment comprises a standard aortic vascular graft in the shape of a human aortic arch. Typically, a human aortic arch has a radius of curvature from about 20 to about 80 millimeters, where "radius of curvature" means a radius of the circle whose curvature matches that of a curve at a particular point. The radius of curvature does not have to be constant along the first segment, and instead can vary along the length thereof to achieve an arcuate shape of desirable configuration.

The first segment has three side branches, preferably in the same plane. A fourth side branch is preferably located at an angle of from 85° to 95°, preferably 89°-91° and still more preferably 90° from the plane of the first three side branches, and is adapted to be joined to a conventional perfusion device such as a heart-lung machine.

The second segment is adapted to be inserted into a patient's open descending aorta and fixed therein as described in detail below, such that the graft's collar portion is positioned at least partially inside the open end or rim of the patient's descending aorta and the entire second segment is contained within the descending aorta.

The second end of the second segment has an initial diameter which is smaller than the diameter of the first segment. More specifically, the second segment of the total aortic replacement graft has an expandable wall whose outer surface is connected to and at least partially covered by an expandable stent. The second segment is adapted to be expanded by a conventional balloon positioned inside the descending aorta and within the graft, as discussed in detail below. When the balloon expands the second segment the stent is expanded also, and the final outside diameter of the second segment is substantially the same as the inner diameter of the patient's aortic wall.

In a preferred embodiment, the initial diameter of the second segment tapers from its first end (joined to the first segment) to the opposite end of the second graft.

The stent is conventional, and may have a repeating "V" arrangement. The stent may be made of stainless steel, nitinol or another biocompatible material.

The expandable stent which at least partially covers the expandable wall of the graft's second segment includes means for attaching the second segment to an internal surface of a patient's descending aorta. These attachment means may be any conventional surgical attachment. In a preferred embodiment, the attachment means comprise a plurality of outwardly radially projecting barbs and/or tines.

The collar is located at the juncture between the first and second segments, and preferably has a width of from 1 to 2 cm and a thickness of from 2 to 5 mm. The collar is made of a material which is suturable to the descending aorta. By "suturable to the descending aorta" it is meant a soft, non-dense material which can be attached to the aortic wall using surgical sutures, has good hemostatic properties and which is capable of distributing suture tension throughout the collar. Polyester fabric, such as polyester felt, is preferred.

The collar includes means for attaching the collar to the rim of a patient's open descending aorta. In a preferred embodiment, the attachment means comprise a plurality of interrupted (as opposed to continuous), non-absorbable sutures fixed at pre-positioned points around an outside circumference of the collar. Typically, the collar has from 6 to 18 non-absorbable sutures. In a preferred embodiment, the sutures are double-armed, arranged at equidistant points along the collar's outer circumference, and pass through the collar in a U-stitch (transverse or horizontal mattress) suture pattern.

The total aortic replacement graft has dimensions which are similar to a patient's aortic arch. In a preferred embodiment, the first segment has a length of 25 to 34 cm and a diameter of 24 to 34 mm, with its hollow cylindrical branches having a length ranging from 15 to 20 cm and a diameter of from 8 to 12 mm.

FIG. 1 illustrates a preferred embodiment of the total aortic replacement arch graft of the present invention. Graft 10 comprises a first segment 20 connected to second segment 30. First segment 20 includes three hollow cylindrical side branches 40, 50 and 60 in the same or substantially the same plane with one another and adapted to be joined to a patient's left subclavian artery, left common carotid artery and innominate artery, respectively. A fourth hollow cylindrical side branch 70 is located substantially 90° from side branches 40, 50 and 60, and is adapted to be joined to a heart-lung machine (not shown).

First segment 20 is joined on its distal end to second segment 30. The second end 80 of second segment 30 is adapted to be inserted into the descending aorta of a patient (not shown). The second segment has an expandable wall 90 whose outer surface is at least partially covered with an expandable open-mesh stent 100. A plurality of tines 110 project outwardly from stent 100.

Collar 120 is located at the juncture between first segment 20 and second segment 30, and has a plurality of non-absorbable sutures 130 fixed at equidistant points along its circumference.

Figure 2:
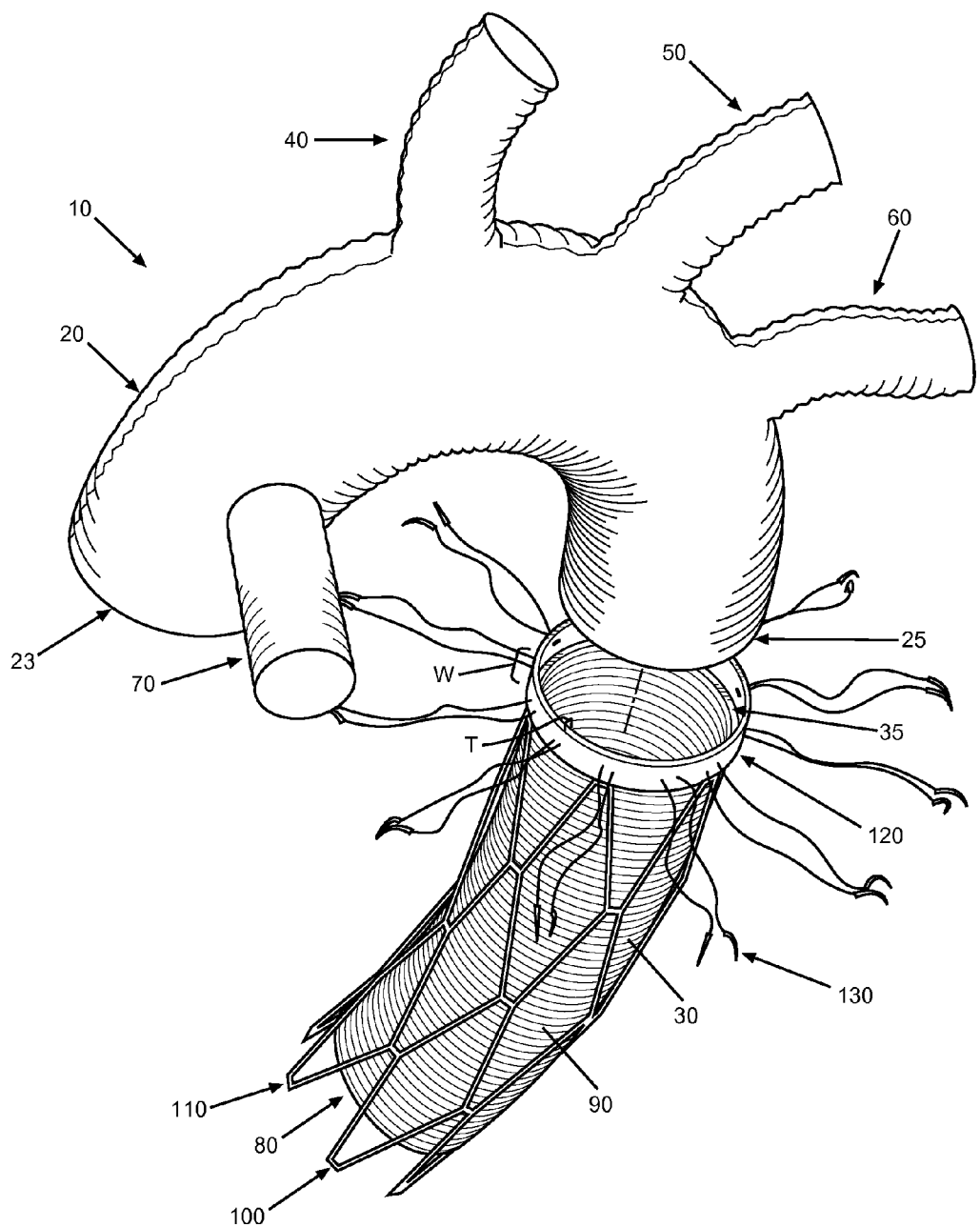
FIG. 2 is an exploded view of the total aortic arch replacement graft illustrated in FIG. 1.

FIG. 2 is an exploded view of the graft illustrated in FIG. 1. FIG. 2 additionally illustrates first end 23 and second end 25 of first segment 20, and first end 35 of second segment 30. Letters T and W refer to the thickness and width, respectively, of collar 120.

Figure 3:
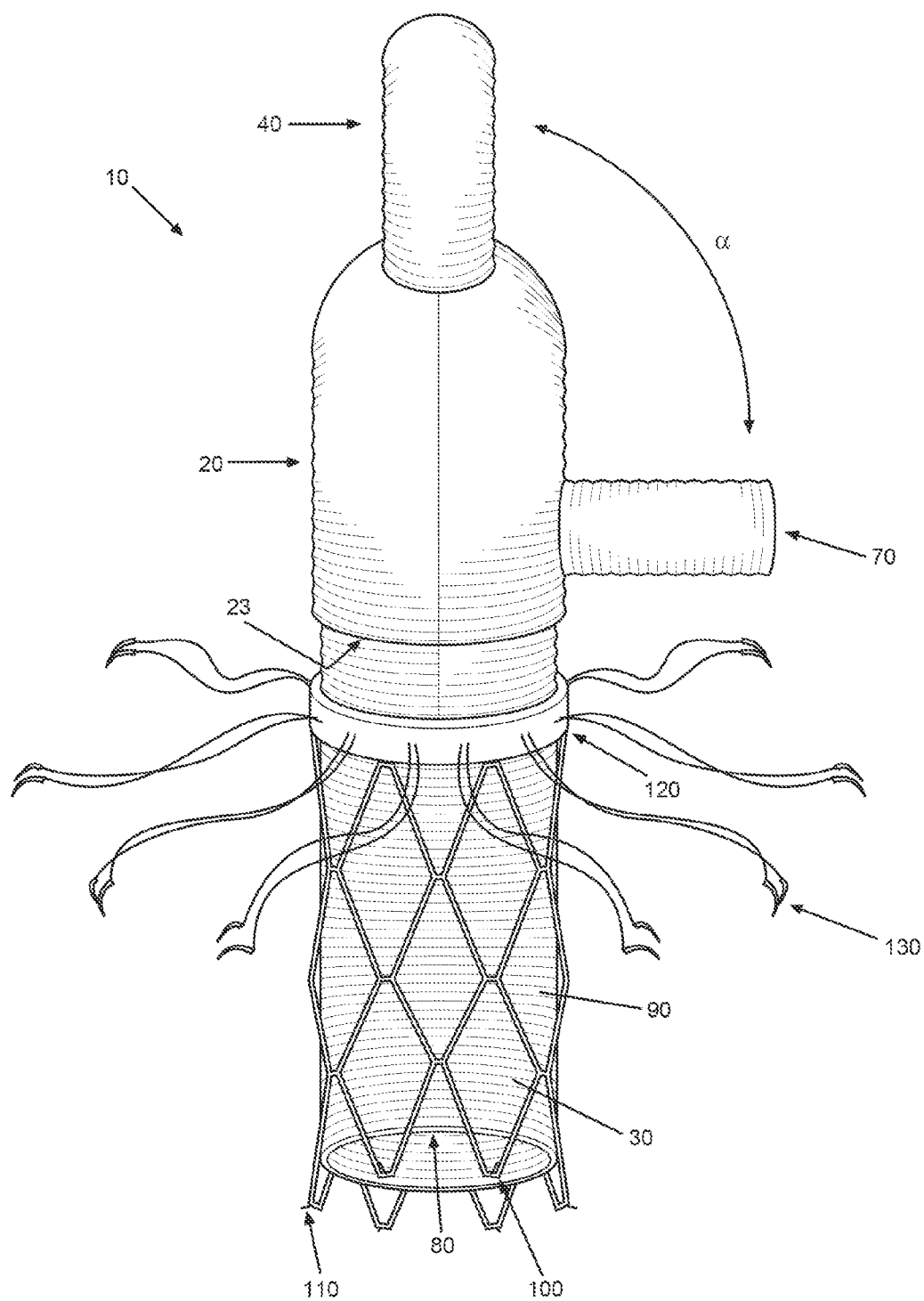
FIG. 3 is an front view of the total aortic arch replacement graft illustrated in FIG. 1.

FIG. 3 is a front view of the graft illustrated in FIG. 1. FIG. 3 additionally illustrates the angle α between side branch 70 and the plane of side branches 40, 50 and 60. The angle α is from 85° to 95°, preferably 89° to 91° and most preferably 90° from the plane of side branches 40, 50 and 60.

The graft of the present invention may be attached to the aorta using conventional surgical techniques such as suturing. Suturing techniques include everting mattress sutures, non-everting mattress sutures, figure eight sutures and continuous sutures.

A preferred method of surgically implanting the total aortic graft of the present invention will now be described. The patient is placed in the supine position and prepped in standard fashion, including cooling his core temperature to 20-25° C. and systemic heparinization at conventional dosages for cardiopulmonary bypass.

A conventional median sternotomy incision is made and the pericardium is opened in the usual fashion. Identification and meticulous dissection and exposure of the ascending aorta, aortic arch, innominate artery, left common carotid artery, left subclavian artery, innominate vein, left vagus nerve and the left recurrent laryngeal nerve is performed. A guide-wire is introduced percutaneously into the common femoral artery, preferably under trans-esophageal echocardiography (TEE) guidance, and extended into the true aortic lumen until it arrives at a mid-arch position.

The right axillary artery is exposed and one efferent limb of a standard bifurcated vascular graft is anastomosed in an end-to-side fashion to a small arteriotomy in the axillary artery. The graft is carefully de-aired and all limbs clamped.

Cannulae are placed in the distal ascending aorta and right atrium, and preferably secured by purse-string sutures using conventional techniques. The arterial return cannula is then connected to the afferent limb of the Y-attachment of the arterial line, while one efferent limb is connected to the afferent limb of the bifurcated vascular graft previously anastomosed to the right axillary artery. At this point the other efferent vascular graft limb may be anastomosed to the left common carotid artery. This may be necessary where there is an incomplete arterial Circle of Willis in order to avoid unequal cerebral perfusion.

Cardiopulmonary bypass is then initiated, draining the systemic venous return through the dual-stage venous cannula in the right atrium and providing systemic arterial perfusion simultaneously through the right axillary as well as aortic cannula. In some cases, cannulation of the ascending aorta can be omitted and replaced by antegrade systemic perfusion through the axillary/innominate artery and hence to the aortic arch.

Myocardial protection is maintained throughout this procedure by using cold blood cardioplegia administered in the retrograde fashion via a catheter placed in the coronary sinus through the free wall of the right atrium, supplemented by systemic cooling to a core temperature of 20-25° C. Snares comprising umbilical tapes are passed around the three arch vessels and passed through tourniquets.

At this point, a standard 40 cc balloon is passed over the previously-placed guide-wire and positioned in the proximal part of the descending thoracic aorta under intraoperative TEE guidance.

Once the desired core temperature is reached, the cardiopulmonary bypass pump flow is reduced to 20 ml/Kg/minute, the aortic perfusion arterial line is clamped, and the snares around the aortic arch branches are tightened, thus initiating hypothermic systemic circulatory arrest with continuous low-flow antegrade regional perfusion.

The aorta is opened, and the entire aortic arch removed by transecting the innominate artery, left common carotid artery and left subclavian arteries. Obviously, the aortic cannula is also removed.

The second segment of the graft is then advanced into the open end of the descending aorta, with the guide-wire positioned inside the graft lumen. The graft is positioned so that its collar is just inside the open edge of the descending aorta. The double armed sutures are passed through the full thickness of the native aortic wall, then through individual felt pledgets or through a narrow felt strip, and tied, thus securing the second segment of the graft inside the native descending aorta, and completing the elephant trunk phase of the procedure.

The efferent limb of the arterial line Y-connection is then disconnected from the aortic cannula and connected to the side-arm of the graft. The proximal end of the first segment of the graft is now clamped. Cardiopulmonary bypass pump flow is then restored to full flow of approximately 150-200 ml/Kg/min through the graft.

The patient may be gradually rewarmed while reconstruction of the arch vessels is performed by individually anastomosing the innominate artery, left common carotid artery and left subclavian artery each to one side branch of the graft in an end-top-end manner. The vascular grafts are carefully de-aired before the snares are loosened and the umbilical tapes removed. At this point, the arterial perfusion limb connected to the bifurcated graft and/or the two efferent limbs attached to the innominate and left common carotid arteries are clamped, transected close to the head vessels and the stumps over-sewn, thereby re-establishing a normal pattern of antegrade perfusion through the reconstructed aortic arch.

Under intraoperative TEE guidance or by intra-operative fluoroscopy, the previously-placed intra-aortic balloon is carefully advanced over the guide-wire until the balloon is positioned completely within the second segment of the graft. When the proper position and alignment are achieved, the balloon is inflated, preferably manually using a large syringe filled with normal saline solution. The inflating balloon urges the second segment's open-mesh stent against the patient's aortic wall, with the stent's barbs further securing the graft's second segment in place. The balloon is then deflated and withdrawn.

Proximal aortic anastomosis is now performed in an end-to-end manner between the open end of the ascending aorta and the proximal end of the first segment of the graft. Weaning from cardiopulmonary bypass is then achieved, strict surgical hemostasis is established, and the wound closed in conventional manner.

A conventional cardiopulmonary bypass pump with its attendant pump lines may be used in the above procedure, with two sequential Y-attachments for arterial return.

The above surgical procedure is illustrative only, and may be altered by those of ordinary skill in cardiac surgery to address the specific presentations of individual patients without departing from the scope of the present invention.

The total aortic arch graft of the present invention provides significant advantages over known aortic grafts, including Minimal Bleeding—The total aortic arch graft minimizes bleeding from the suture line due to its one-piece construction and reduced number of sutures.

Precise Placement—The one-piece construction of the total aortic arch graft allows quick, precise and secure placement of the graft at a desired location within the descending aorta using simple and easy surgical procedures.

Reduced Deep Hypothermic Arrest—The total aortic arch graft reduces the period of time a patient must spend in deep hypothermic circulatory arrest, and the level of hypothermic circulatory arrest, while his aortic arch is replaced.

Quicker Systemic Perfusion—The total aortic arch graft permits quicker resumption/re-establishment of systemic perfusion than permitted by known grafts.

The invention claimed is:

1. A total aortic arch reconstruction graft, comprising
a) a first, hollow cylindrical segment in the shape of an aortic arch and having first and second opposed ends and a pre-determined diameter,
said first segment having three hollow cylindrical side branches in communication therewith, said three side branches in the same or substantially the same plane with one another and adapted to be joined to a patient's left subclavian artery, left common carotid artery and innominate artery, respectively,
said first segment having a fourth hollow cylindrical side branch adapted to be joined to a perfusion device;
said first end of said first segment being adapted to be joined to a cut end of an ascending aortic wall of a patient;
b) a second, hollow cylindrical segment having first and second opposed ends,
the first end of said second segment being joined to said second end of said first segment,
the second end of said second segment adapted to be inserted into the descending aorta of a patient, said second segment having an expandable wall whose outer surface is at least partially covered with an expandable stent, said stent having means for attaching said second segment to an internal surface of a patient's descending aorta,
an initial diameter of said second end of said second segment being smaller than said pre-determined diameter of said first segment;
c) a collar having a diameter larger than the pre-determined diameter of said first segment, said collar located at a juncture where the first end of said second segment is joined to the second end of said first segment, and incorporating a plurality of separate, non-absorbable, double-armed sutures pre-attached at points around an outside circumference of said collar for attaching said collar to an open end of a patient's descending aorta.

2. The graft of claim 1, wherein said means for attaching said second segment is a member selected from the group consisting of barbs and tines.

3. The graft of claim 1, wherein the plurality of sutures comprises 6-18 non-absorbable doubled-armed sutures.

4. The graft of claim 1, wherein said first and second segments are both made of a material selected from the group consisting of nylon, polyester, polyolefin, polyurethane, polytetrafluoroethylene, and mixtures thereof.

5. The graft of claim 4, wherein the polyester is a polyester selected from the group consisting of woven polyester, double-velour woven polyester, knitted polyester, albumen coated woven polyester and albumen coated knitted polyester.

6. The graft of claim 1, wherein said collar has a width of from 1 to 2 cm and a thickness of from 2 to 5 mm.

7. The graft of claim 1, wherein said collar comprises a polyester felt.

8. The graft of claim 1, wherein said first segment is 25 to 34 cm in length.

9. The graft of claim 1, wherein a diameter of each said hollow cylindrical side branches is from 8 to 12 mm.

10. The graft of claim 1, wherein a length of said hollow cylindrical side branches ranges from 15 to 20 cm.

11. The graft of claim 1, wherein a diameter of said first segment is 24 to 34 mm.

12. The graft of claim 1, wherein said fourth side branch is located at an angle of from 85° to 95° from the plane of the three side branches.

13. The graft of claim 12, wherein said angle is from 89° to 91°.

14. The graft of claim 13, wherein said angle is 90°.

15. The graft of claim 1, wherein said graft has a one-piece construction.

* * * * *